US00PP22784P2

(12) United States Plant Patent
Smith

(10) Patent No.: US PP22,784 P2
(45) Date of Patent: Jun. 12, 2012

(54) ***CHRYSANTHEMUM* PLANT NAMED 'SYWAN PUR'**

(50) Latin Name: *Chrysanthemum×morifolium*
Varietal Denomination: Sywan Pur

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/065,999

(22) Filed: Apr. 4, 2011

(51) Int. Cl.
*A01H 5/00* (2006.01)

(52) U.S. Cl. ..... Plt./287

(58) Field of Classification Search ..... Plt./287, Plt./292
See application file for complete search history.

*Primary Examiner* — Kent L Bell
(74) *Attorney, Agent, or Firm* — Joshua L. Price

(57) ABSTRACT

A new *Chrysanthemum* plant named 'Sywan Pur' particularly distinguished by the bold red-purple inflorescence color, medium green foliage, rounded and mounded plant habit, and a natural flowering season response that is about early October.

1 Drawing Sheet

Latin name of the genus and species of the plant claimed: *Chrysanthemum×morifolium.*

Varietal denomination: 'Sywan Pur'.

BACKGROUND OF THE NEW PLANT

The present invention comprises a new *Chrysanthemum*, botanically known as *Chrysanthemum×morifolium*, and hereinafter referred to by the variety name 'Sywan Pur'.

'Sywan Pur' is a product of a planned breeding program. The new cultivar has bold red-purple inflorescence color, medium green foliage, rounded and mounded plant habit, and a natural flowering season response that is about early October.

'Sywan Pur' originates as a natural whole plant mutation of 'Yowanda', U.S. Plant Pat. No. 20,210. Sywan Pur' was discovered and selected by the inventor as a single flowering plant within a population of the parent cultivar in a controlled breeding program in Alva, Fla. in November 2007. The parent cultivar 'Yowanda' has larger and lighter purple inflorescences and a natural flowering season response that is 3-4 days faster.

The first act of asexual reproduction of 'Sywan Pur' was accomplished when vegetative cuttings were propagated from the initial selection in December 2007 in a controlled environment in Alva, Fla.

BRIEF SUMMARY OF INVENTION

Horticultural examination of plants grown from cuttings of the plant initiated in December 2007, and continuing thereafter, has demonstrated that the combination of characteristics as herein disclosed for 'Sywan Pur' are firmly fixed and are retained through successive generations of asexual reproduction.

'Sywan Pur' has not been observed under all possible environmental conditions. The phenotype may vary significantly with variations in environment such as temperature, light intensity and day length.

A Plant Breeder's Right for this cultivar was applied for in Canada on Apr. 9, 2010 (No. 10-6934). 'Sywan Pur' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Sywan Pur' with colors being as true as possible with an illustration of this type.

The photographic drawing shows a flowering potted plant of the new variety.

DETAILED BOTANICAL DESCRIPTION

The plant used for the photographs was about 16 weeks old grown in Monroeville, N.J. in an outdoor trial. One rooted cuttings grown in a nine inch pot with no terminal pinching of the apices. The photograph was taken in mid October 2010 in New Jersey.

The plant descriptions and measurements were taken in Gilroy, Calif. in May 2010 under natural light. Plants were grown under conditions which approximate those generally used for potted *chrysanthemum* trials in a greenhouse. These plants used in the descriptions were about 10 weeks old.

Color references are made to The Royal Horticultural Society Colour Chart (R.H.S.) 2001.

TABLE 1

DIFFERENCES BETWEEN THE NEW VARIETY 'SYWAN PUR' AND A SIMILAR VARIETY

| | 'Sywan Pur' | 'Bold Yovanessa' (U.S. Plant Pat. No. 16,581) |
|---|---|---|
| Inflorescence size: | Larger | Smaller |
| Plant habit: | More compact | More upright |

TABLE 1-continued

DIFFERENCES BETWEEN THE NEW VARIETY 'SYWAN PUR' AND A SIMILAR VARIETY

| | 'Sywan Pur' | 'Bold Yovanessa' (U.S. Plant Pat. No. 16,581) |
|---|---|---|
| Natural flowering season response: | Couple days faster | More than a week slower |

Plant:

*Form, growth and habit*.—Herbaceous decorative garden-type, stems upright and outwardly spreading, freely branching, strong and moderately vigorous growth habit.

*Plant height*.—13 cm.

*Plant height* (*inflorescence included*).—20-22 cm.

*Plant width*.—20 cm.

*Garden performance and tolerance to weather*.—Very good.

Roots:

*Number of days to initiate roots*.—4 days at about 22 degrees C.

*Number of days to produce a rooted cutting*.—10-12 days at 22 degrees C.

*Type*.—Fine, fibrous, free branching.

*Color*.—RHS N155B but whiter.

Foliage:

*Arrangement*.—Alternate.

*Immature, leaf color, upper surface*.—Closest to RHS 137A.

*Lower surface*.—Closest to RHS 147B.

*Mature, leaf color, upper surface*.—Closest to RHS 137A.

*Lower surface*.—Closest to RHS 147B.

*Length*.—5.0-5.8 cm.

*Width*.—4.5-4.7 cm.

*Shape*.—Ovate.

*Base shape*.—Attenuate.

*Apex shape*.—Rounded to sometimes mucronulate.

*Margin*.—Irregularly and palmately lobed; serrate.

*Texture, upper surface*.—Bifid T-shaped hairs.

*Lower surface*.—Bifid T-shaped hairs.

*Color of veins, upper surface*.—RHS 138B indistinct terminally.

*Color of veins, lower surface*.—Closest to RHS 138B.

*Petiole color*.—Closest to RHS 138B.

*Length*.—1.7-1.8 cm.

*Diameter*.—0.3-0.4 cm.

*Texture*.—Bifid T-shaped hairs.

Stem:

*Quantity of main branches per plant*.—6-7.

*Color of stem*.—Closest to RHS 146B.

*Length of stem*.—11-13 cm.

*Diameter*.—0.3-0.4 cm.

*Length of internodes*.—0.5-1.5 cm.

*Texture*.—Heavily Bifid T-shaped hairs.

*Color of peduncle*.—Closest to RHS 146B.

*Length of peduncle*.—3.5-4.0 cm.

*Peduncle diameter*.—0.2 cm.

*Texture*.—Bifid T-shaped hairs.

Inflorescence:

*Type*.—Compositae type, solitary inflorescences, decorative-type, borne terminally above foliage, ray florets arranged acropetally on a capitulum.

*Quantity of short days to flowering* (*response time*).—About 49 days.

*Quantity of inflorescences per plant*.—50-55.

*Lastingness of individual blooms on the plant*.—About 6 weeks from first color.

*Fragrance*.—Slightly spicy.

Bud (just when opening/showing color):

*Color*.—Between RHS 70A and RHS 70B.

*Length*.—1.0-1.3 cm.

*Width*.—0.8-1.1 cm.

*Shape*.—Oblate.

Immature inflorescence:

*Diameter*.—3.5 cm.

*Color of ray florets, upper surface*.—Closest to and between RHS 71A and RHS 70A.

*Lower surface*.—Closest to RHS 70A but more gray.

Mature inflorescence:

*Diameter*.—5.5-6.0 cm.

*Depth*.—2.5 cm.

*Total diameter of 'disc'*.—0.1-0.2 cm.

*Receptacle height*.—0.5 cm.

*Receptacle diameter*.—0.6-0.7 cm.

Ray florets:

*Average quantity of florets*.—Approximately 175 in numerous whorls.

*Color of florets, upper surface*.—RHS 70A with slight longitudinal patches of RHS 70B.

*Lower surface*.—Closest to RHS 70B.

*Length*.—2.5-2.8 cm.

*Width*.—0.5-0.65 cm.

*Shape*.—Narrow elliptical.

*Apex shape*.—Praemorse.

*Margin*.—Entire.

*Texture, upper surface*.—Papillose.

*Lower surface*.—Papillose.

Disc florets:

*Average quantity of florets*.—7-10.

*Color of florets*.—RHS 1C basally, RHS 7A apex.

*Length*.—0.4 cm.

*Width*.—0.1 cm.

*Shape*.—Tubular, elongated.

*Apex shape*.—Acute, 5 pointed.

Phyllaries:

*Quantity*.—100-150.

*Color, upper surface*.—RHS 137C.

*Lower surface*.—RHS 137A but some darker.

*Length*.—0.6-0.7 cm.

*Width*.—0.1-0.2 cm.

*Shape*.—Ligulate.

*Apex shape*.—Acute to obtuse.

*Base*.—Fused.

*Margins*.—Entire, papery.

*Texture, upper surface*.—Glabrous.

*Lower surface*.—Bifid T-shaped hairs.

Reproductive organs:

*Pistil*.—1, found on both types of florets.

*Length*.—0.6 cm.

*Style color*.—RHS 1C.

*Style length*.—0.3-0.4 cm.

*Stigma color*.—RHS 7A.

*Stigma shape*.—Bi-parted.

*Ovary color*.—Not observed.

*Stamens*.—4, found on both types of florets.

*Color of filaments*.—RHS 2D.

*Length filaments*.—0.3-0.4 cm.

*Anther color*.—RHS 6A.

*Anther length*.—0.1 cm.

*Anther shape*.—Oval.

*Color of pollen*.—N/A.

*Pollen amount*.—None observed.

*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Sywan Pur' substantially as illustrated and described herein.

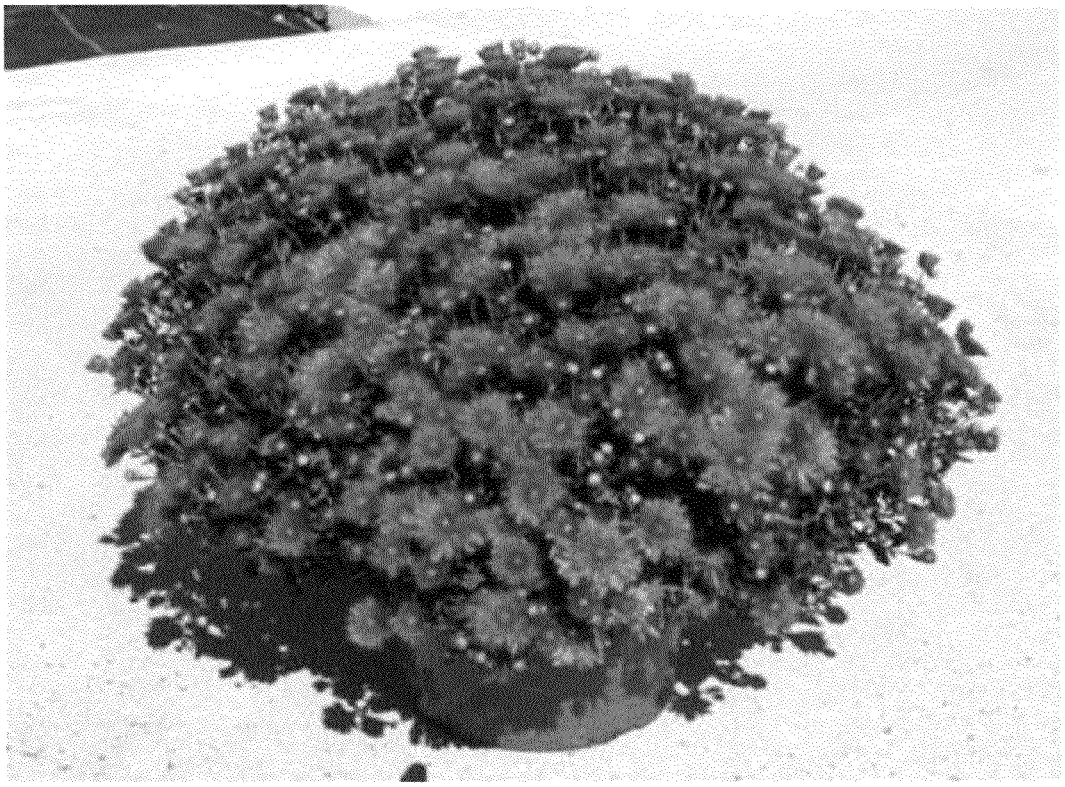

* * * * *